US011930938B1

(12) United States Patent
Elliott et al.

(10) Patent No.: US 11,930,938 B1
(45) Date of Patent: Mar. 19, 2024

(54) FALL PREVENTION BARRIER

(71) Applicants: Josh Elliott, Ivoryton, CT (US);
Vinneth Carvalho, Ivoryton, CT (US)

(72) Inventors: Josh Elliott, Ivoryton, CT (US);
Vinneth Carvalho, Ivoryton, CT (US)

( * ) Notice: Subject to any disclaimer, the term of this patent is extended or adjusted under 35 U.S.C. 154(b) by 336 days.

(21) Appl. No.: 17/517,856

(22) Filed: Nov. 3, 2021

(51) Int. Cl.
*A47D 15/00* (2006.01)
*A61M 21/02* (2006.01)
*A61M 21/00* (2006.01)

(52) U.S. Cl.
CPC ......... *A47D 15/005* (2013.01); *A47D 15/008* (2013.01); *A61M 21/02* (2013.01); *A61M 2021/0027* (2013.01); *A61M 2021/0044* (2013.01)

(58) Field of Classification Search
CPC .... A47D 15/005; A47D 15/008; A47D 15/00; A61M 21/02; A61M 2021/0027; A61M 2021/0044; A61M 2021/0005
USPC ............ 5/427, 428, 425, 424, 655, 657, 652
See application file for complete search history.

(56) References Cited

U.S. PATENT DOCUMENTS

| | | | |
|---|---|---|---|
| 2,626,407 A * | 7/1953 | Kurry | A47D 15/003 5/655 |
| 4,681,195 A * | 7/1987 | Trahan | A45C 9/00 135/117 |
| 5,056,533 A * | 10/1991 | Solano | A61G 7/1023 5/655 |
| 5,103,514 A * | 4/1992 | Leach | A47D 13/08 5/655 |
| 5,233,710 A * | 8/1993 | Bernard | A47D 7/04 5/426 |
| 5,357,642 A * | 10/1994 | Clute | A47D 13/08 5/904 |
| 5,473,785 A * | 12/1995 | Lager | A47D 9/005 5/655 |
| 5,956,787 A | 9/1999 | James | |
| 6,408,463 B1 * | 6/2002 | Palacio | A47D 15/003 5/655 |
| 6,721,974 B1 | 4/2004 | Wilkinson | |
| 6,823,543 B2 * | 11/2004 | Diak/Ghanem | A47G 9/02 5/946 |
| 7,346,949 B2 * | 3/2008 | Kamrin-Balfour | A47D 15/003 5/904 |
| 7,549,183 B2 * | 6/2009 | Dockendorf | A47D 11/00 5/640 |
| 7,587,772 B2 * | 9/2009 | Ward | A47D 13/066 5/904 |

(Continued)

*Primary Examiner* — Robert G Santos
(74) *Attorney, Agent, or Firm* — Sanchelima & Associates, P.A.; Christian Sanchelima; Jesus Sanchelima

(57) ABSTRACT

A fall preventing barrier including a base assembly, a barrier assembly, a soothing assembly, and a cover assembly is disclosed herein. The base assembly includes a base that is configured to be placed on top of a mattress or on the floor. A plurality of barriers from said barrier assembly are mounted on top of said base, covering both lateral sides and a top side. The plurality of barriers is configured to impede a person from falling from a bed. The soothing assembly includes a plurality of lights, a plurality of voice recorders and a book holder to provide comfort. The soothing assembly is mounted on said plurality of barriers. Said cover assembly includes a cover that envelop the base assembly and the barrier assembly. The fall preventing barrier can be folded in order to be stored easily.

2 Claims, 6 Drawing Sheets

(56) References Cited

U.S. PATENT DOCUMENTS

| | | | | |
|---|---|---|---|---|
| 7,856,688 B2* | 12/2010 | Dockendorf | ............. | A45C 9/00 5/655 |
| 10,918,223 B2* | 2/2021 | Goodwin | ............. | A47D 15/005 |
| 2004/0064889 A1* | 4/2004 | Diak/Ghanem | .......... | A47G 9/02 5/733 |
| 2005/0210592 A1* | 9/2005 | Littlehorn | ............ | A47D 15/003 5/655 |
| 2006/0010604 A1* | 1/2006 | Kamrin-Balfour | .......................... | A47D 15/008 5/904 |
| 2006/0010605 A1* | 1/2006 | Kamrin-Balfour | .......................... | A47D 15/003 5/904 |
| 2006/0075563 A1* | 4/2006 | Bartner | ................ | A47D 13/083 5/655 |
| 2007/0079444 A1* | 4/2007 | Ward | ................... | A47D 15/003 5/904 |
| 2007/0163051 A1* | 7/2007 | Straub | .................... | A47D 13/08 5/655 |
| 2007/0220679 A1* | 9/2007 | Dockendorf | ......... | A47D 15/008 5/655 |
| 2007/0245494 A1* | 10/2007 | Dockendorf | ......... | A47D 13/083 5/655 |
| 2008/0172795 A1* | 7/2008 | Straub | .................. | A47D 15/008 5/655 |
| 2018/0338628 A1* | 11/2018 | Goodwin | ............. | A47D 15/008 |

* cited by examiner

FALL PREVENTION BARRIER

BACKGROUND OF THE INVENTION

1. Field of the Invention

The present invention relates to a fall prevention barrier and, more particularly, to a fall prevention barrier that prevent a person from falling out of a bed.

2. Description of the Related Art

Several designs for a fall prevention barrier have been designed in the past. None of them, however, include a mattress cover with elevated foam barriers around the perimeter.

Applicant believes that a related reference corresponds to U.S. Pat. No. 5,956,787 issued for a pneumatic mattress assembly that is placed over a traditional mattress and has inflatable side walls that prevent a person from falling out of a bed. Applicant believes that another related reference corresponds to U.S. Pat. No. 6,721,974 issued for a safety barrier for beds which prevents a person from falling from the bed. None of these references, however, teach of a fall prevention barrier that includes a mattress cover with elevated foam barriers around the perimeter that prevent a person from falling out of a bed, the fall preventing barrier also includes reading lights, a music generator and a pocket for holding books.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a fall preventing barrier that keeps a person on a bed with soft barriers so that the person does not get bruised if he hits the barriers when moving around.

It is another object of this invention to provide a fall preventing barrier that is lightweight, therefore, can be transported easily, suitable for sleepovers and camping.

It is still another object of the present invention to provide a fall preventing barrier that can be used on top of a bed or on the floor.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
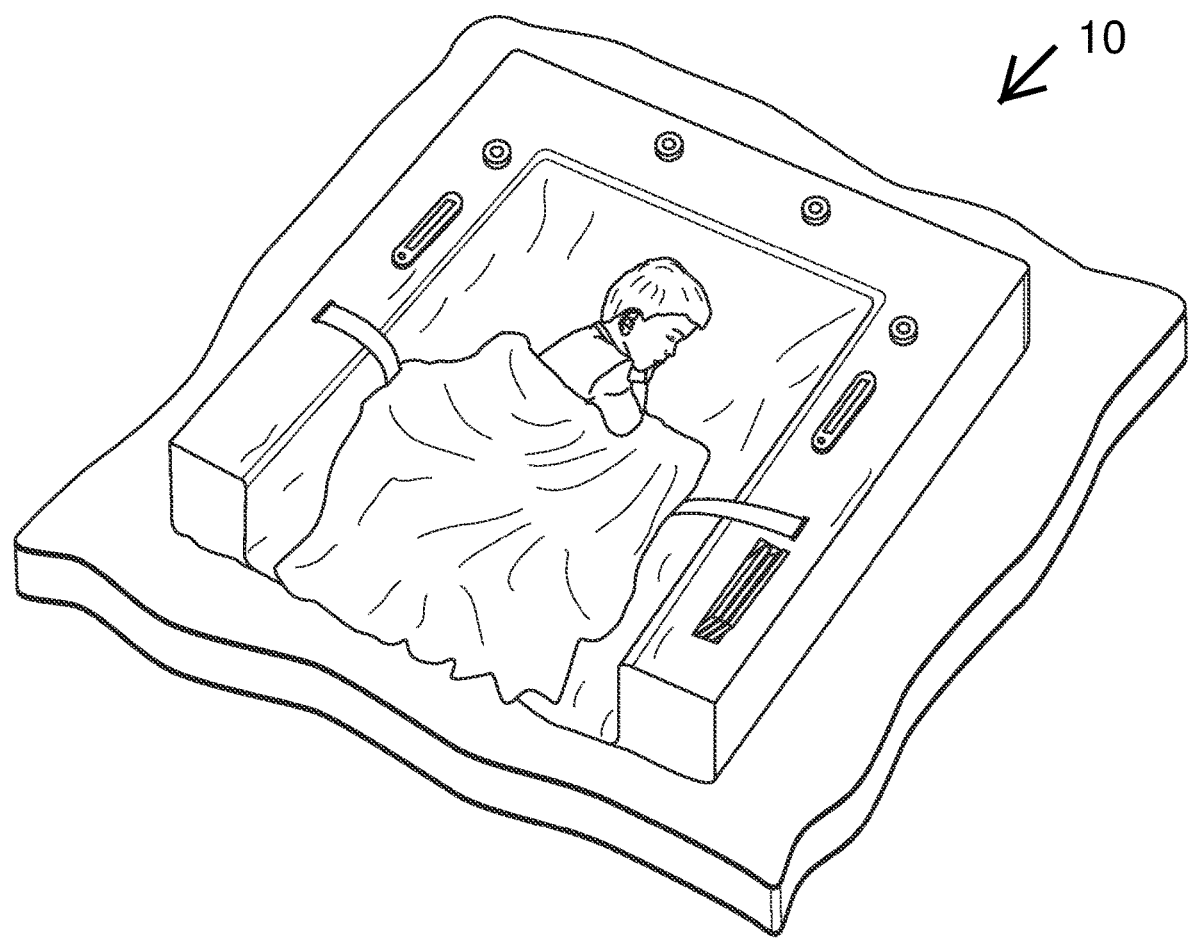
FIG. 1 represents an isometric operational view of the present invention 10.
Figure 2:
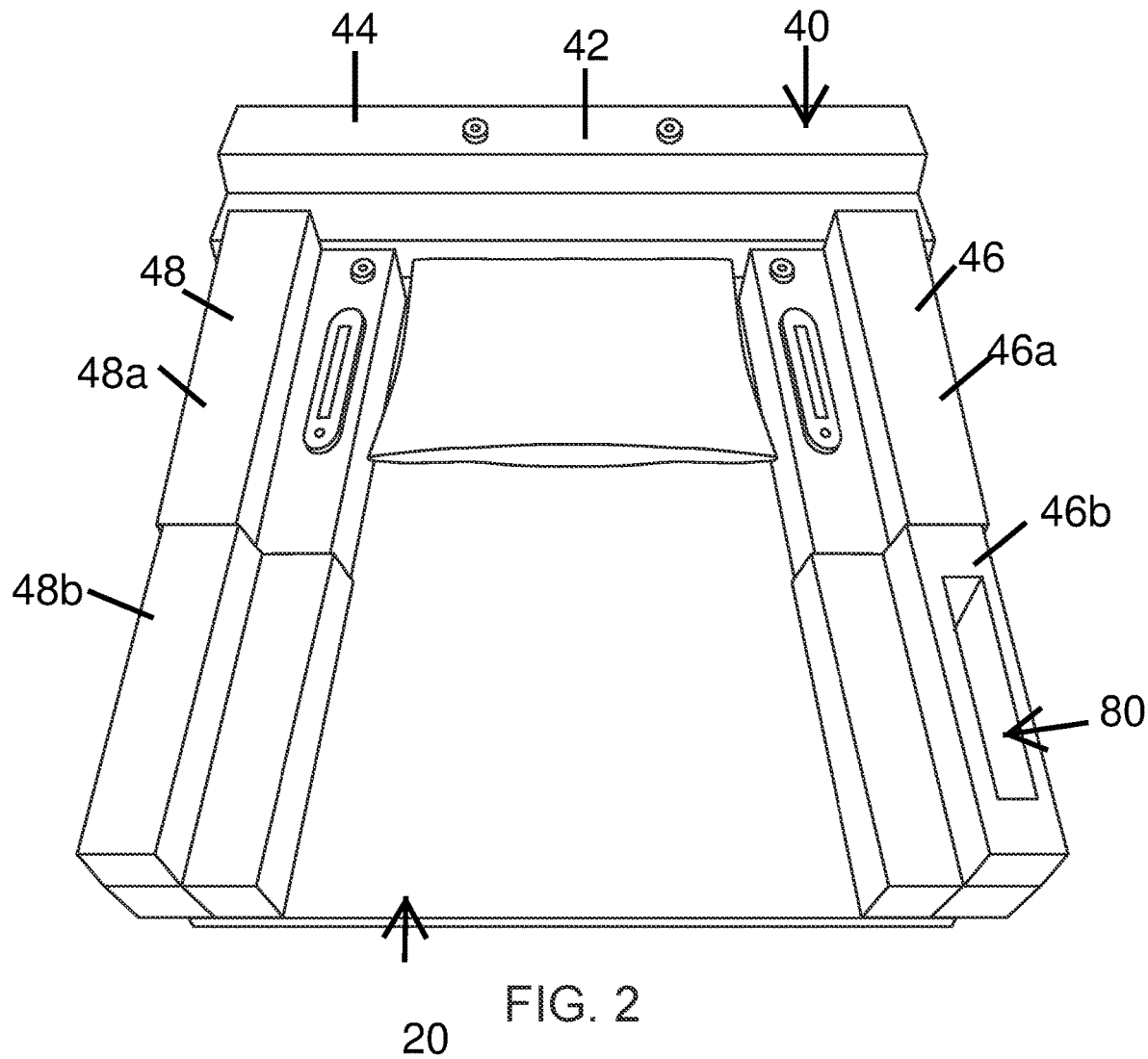
FIG. 2 shows a front view of the present invention 10 depicting the base assembly 20, the barrier assembly 40, and the soothing assembly 80. The barrier assembly 40 includes a plurality of barriers 42 that form a top barrier 44, a right lateral barrier 46 and a left lateral barrier 48.

Referring now to the drawings, where the present invention is generally referred to with numeral 10, it can be observed that it basically includes a base assembly 20, a barrier assembly 40, a fastening assembly 60, a soothing assembly 80, and a cover assembly 90. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The base assembly 20 includes a first base layer 22 and a second base layer 24. Said first base layer 22 may have a rectangular shape, nonetheless, in other embodiments said first base layer 22 may have a quadrangular shape, a circular shape, a triangular shape, an irregular shape, or any variation thereof. In a suitable embodiment said first base layer 22 may be made of cardboard. In other embodiments said first base layer may be made of plastic, wood, paperboard, or any variation of the like. Said first base layer 22 may be used to give the fall prevention barrier 10 a strong and solid base. Said second base layer 24 includes a top distal end 24a, a right distal end 24b, and a left distal end 24c. Said second base layer 24 may have a rectangular shape, however, in other embodiments said second base layer 24 may have a triangular shape, quadrangular shape, circular shape, oval shape, irregular shape, or any variation thereof. In a suitable embodiment said second base layer 24 may be made of memory foam. In other embodiments said second base layer may be made of lux foam, latex foam, polyurethane foam, polyether foam, polyester foam, or any variation thereof. Said second base layer 24 may be used to give a soft surface to the fall prevention barrier 10. The second base layer 24 may be mounted onto said first layer base 22. In conjunction said first base layer 22 and said second base layer 24 may provide a solid and soft base to the fall prevention barrier 10.

The barrier assembly 40 includes a plurality of barriers 42: a top barrier 44, a right lateral barrier 46, and a left lateral barrier 48. Each barrier from said plurality of barriers 42 may have a cuboid shape. In other embodiments each barrier may have a cylindrical shape, a triangular prism shape, a pentagonal prism shape, or any other variation of an elongated prism. Said plurality of barriers 42 may be made of lux foam, latex foam, polyurethane foam, polyether foam, polyester foam, or any variation thereof. In a suitable embodiment each barrier from said plurality of barriers may be a square pool noodle. The top barrier 44 may be composed by said plurality of barriers 42. Said top barrier 44 may be an elevated barrier. Said top barrier 44 may be mounted onto said top distal end 24a. The barriers that may compose the top barrier 44 may be placed horizontally onto said top distal end 24a. In a suitable embodiment a first barrier from said plurality of barriers may be placed horizontally onto said top distal end, a second barrier from said plurality of barriers 42 may be mounted on top of said first barrier. In other embodiments the top barrier 44 may have a different configuration like being composed of more than two barriers, the barriers may be placed vertically, or any variation. The right lateral barrier 46 further includes a first right section 46a and a second right section 46b. The right lateral barrier 46 may be composed of said plurality of barriers 42. Said right lateral barrier 46 may be mounted onto said right distal end 24b. In a suitable embodiment said right lateral barrier 46 may be composed of six barriers from said plurality of barriers 42. Said first right section 46a may include three barriers, two of the barriers may be arranged to be coplanar and sequentially mounted adjacent to each other about a lateral edge, a third barrier may be mounted on top of said two barriers. Said second right section 46b may include three barriers, two of the barriers may be arranged to be coplanar and sequentially mounted adjacent to each other about a lateral edge, a third barrier may be mounted on top of said two barriers. The left lateral barrier 48 further includes a first left section 48a and a second right section 48b. The left lateral barrier 48 may be composed of said plurality of barriers 42. Said left lateral barrier 48 may be mounted onto said left distal end 24c. In a suitable embodiment said left lateral barrier 48 may be composed of six barriers from said plurality of barriers 42. Said first left section 48a may include three barriers, two of the barriers may be arranged to be coplanar and sequentially mounted adjacent to each other about a lateral edge, a third barrier may be mounted on top of said two barriers. Said second left section 48b may include three barriers, two of the barriers may be arranged to be coplanar and sequentially mounted adjacent to each other about a lateral edge, a third barrier may be mounted on top of said two barriers.

The fastening assembly 60 includes a plurality of fasteners 62, and a plurality of straps 64. Said plurality of fasteners 62 may be used to join said first base layer 22 with said second base layer 24. Said plurality of fasteners 62 may be used to join the plurality of barriers 42 to form said top barrier 44, said right lateral barrier 46, and said left lateral barrier 48. Said plurality of fasteners 62 may be used to join said top barrier 44 with said top distal end 24a, said right lateral barrier 46 with said right distal end 24b, and said left lateral barrier 48 with said left distal end 24c. In a preferable embodiment each fastener from said plurality of fasteners 62 may be a hook and loop fastener, nevertheless, other fasteners may be suitable for this purpose such as snap fasteners, safety pins, zippers, or any variation of the like. A first strap from said plurality of straps 64 may be attached to said second right section 46b. A first strap from said plurality of straps 64 may be attached to said second right section 46b. A second strap from said plurality of straps 64 may be attached to said second left section 48b. The plurality of straps 64 may be configured to fasten a user while sleeping.

Figure 3:
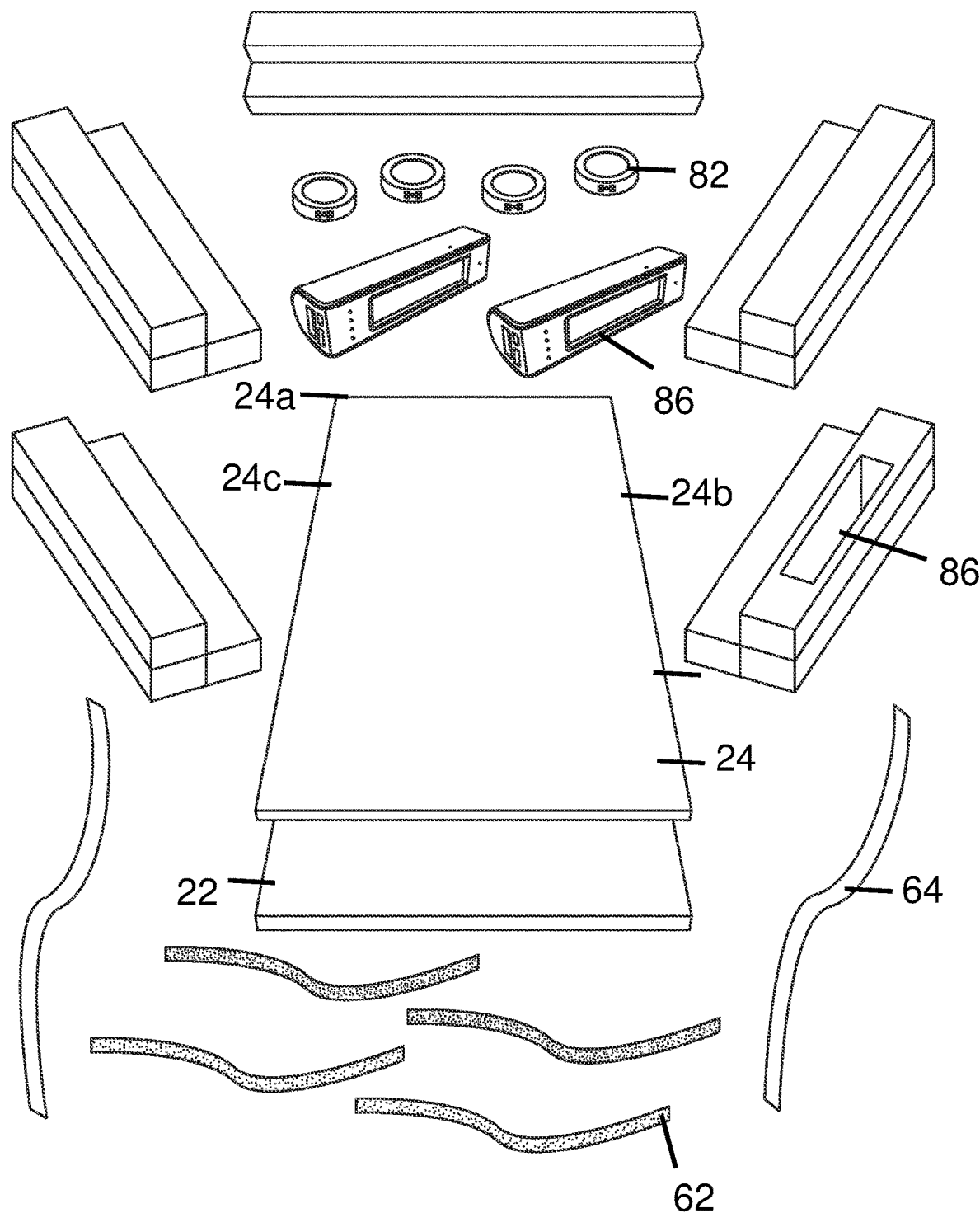
FIG. 3 illustrates an exploded view of the base assembly 20, the barrier assembly 40, the fastening assembly 60, and soothing assembly 80.
Figure 4:
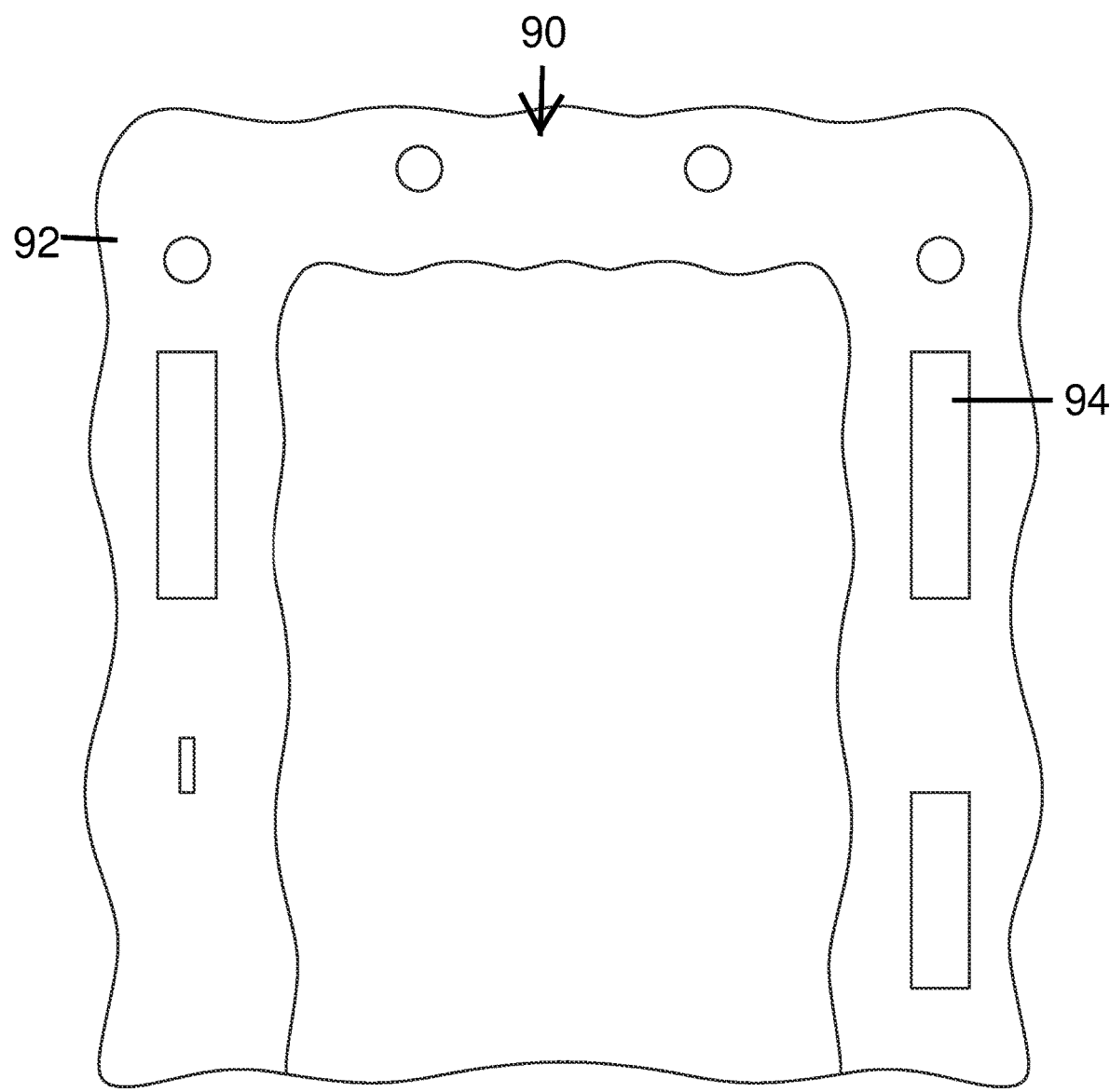
FIG. 4 is a representation of the cover assembly 90. It is represented a cover 92 with a plurality of openings 94.
Figure 5:
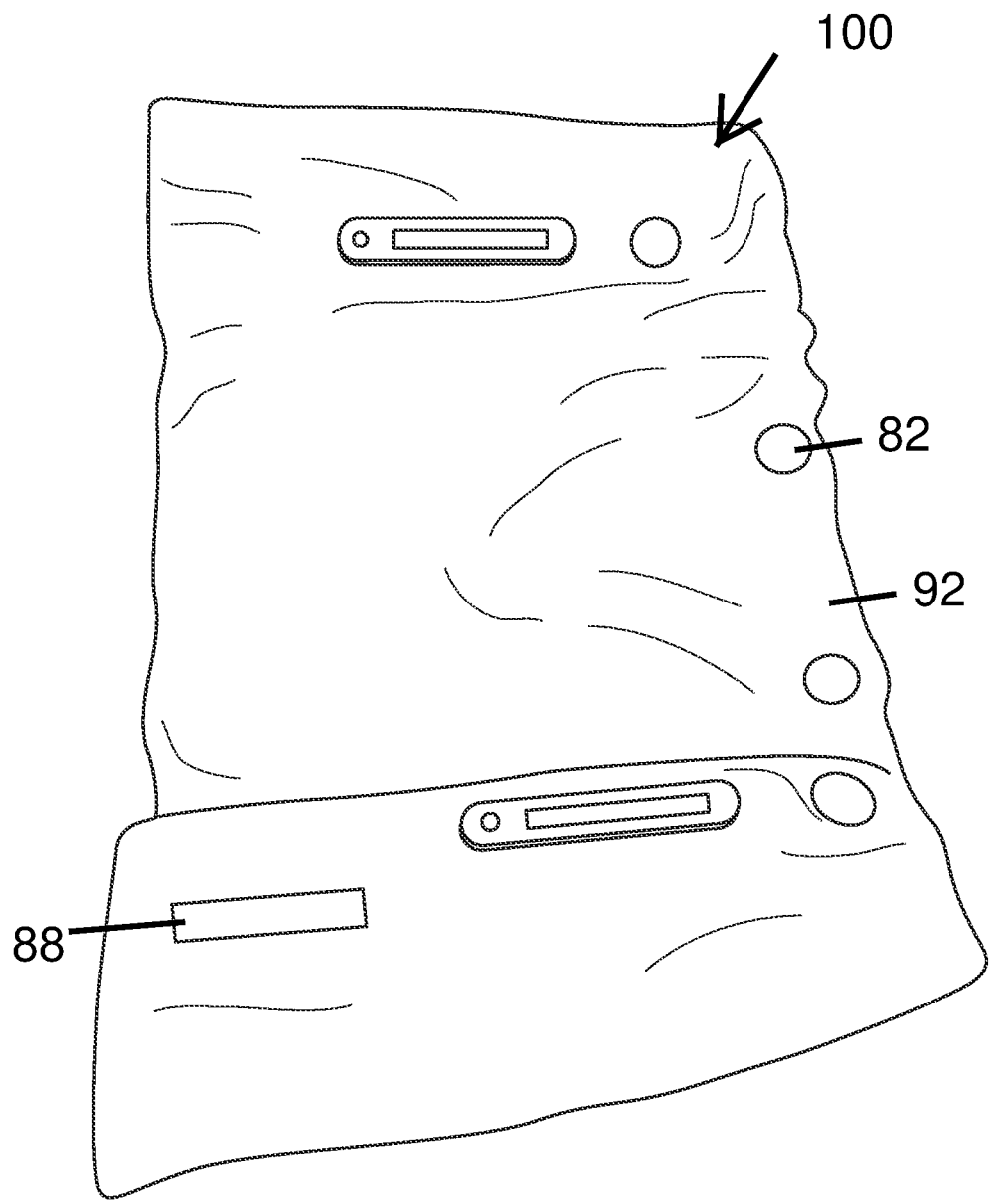
FIG. 5 illustrates an isometric view of the present invention in a folded configuration 100.
Figure 3:
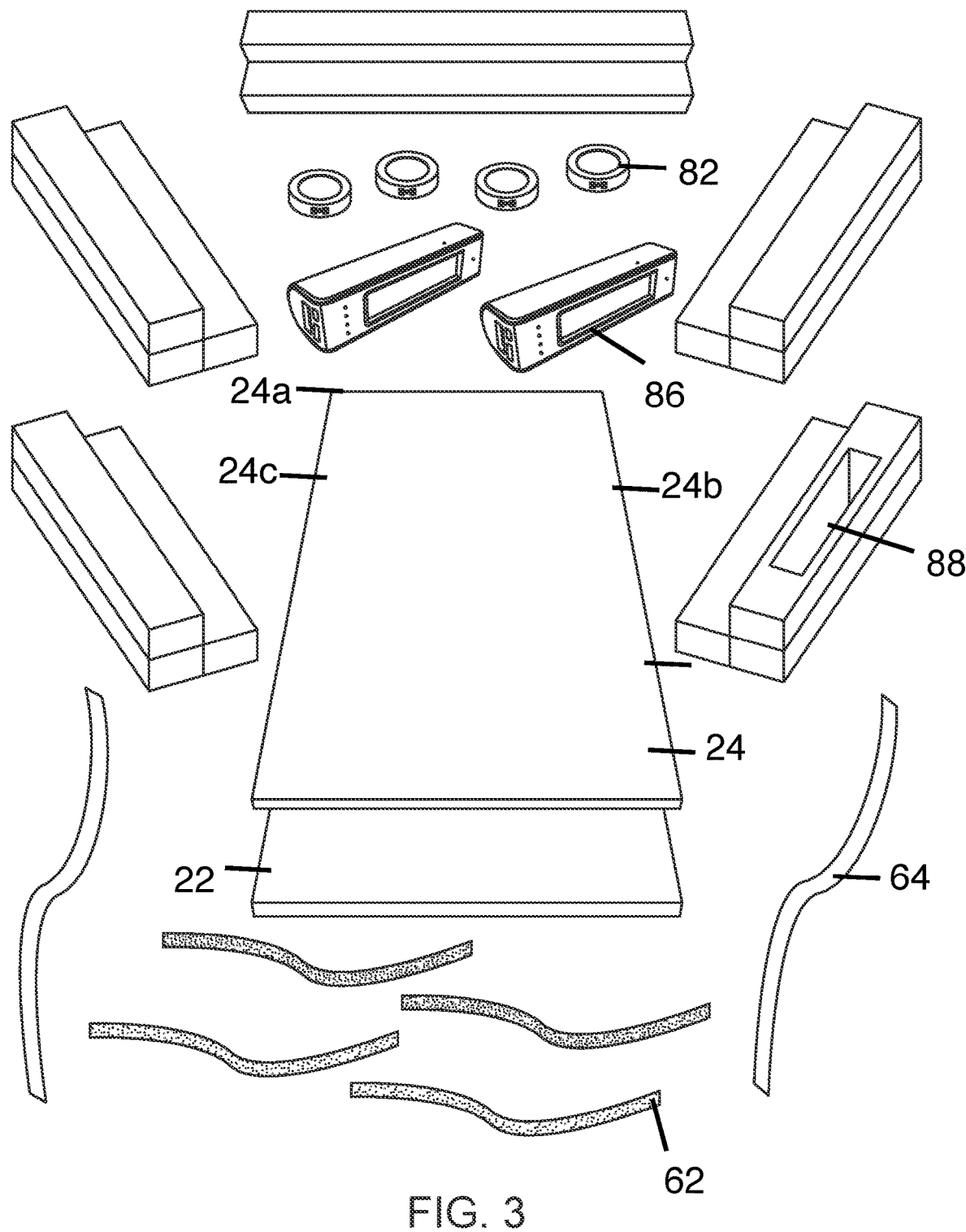

The soothing assembly 80 includes a plurality of lights 82, a pillow 84, a plurality of voice recorders 86, and a book holder 88. Said soothing assembly 80 may be configured to provide comfort to a user when the fall prevention barrier 10 may be used. In a suitable embodiment each light from said plurality of lights 82 may be a cordless led light as depicted in FIG. 3. In other embodiments each light from said plurality of lights 82 may be light bulbs, neon lights, fluorescent tubes, or any variation thereof. Said plurality of lights 82 may be located on said top barrier 44, on said first right section 46a, and on said first left section 48a. However, said plurality of lights 82 may be located wheresoever in said barrier assembly 40. Said pillow 84 may be filled with shredded memory foam and cotton, other materials may be used for this purpose. Said plurality of voice recorders 86 may be located on said first right section 46a, and on said first left section 48a. Said plurality of voice recorders 86 may be used to play songs, lullabies, audiobooks, or any variation of the like. Said book holder 88 may have rectangular shape. Said book holder 88 may be volumetrically suitable to partially enclose books that may have different shapes and sizes. Said book holder 88 may be located in said second right section 46b, nonetheless, said book holder 88 may be located wheresoever in said barrier assembly 40.

The cover assembly 90 includes a cover 92. In a suitable embodiment said cover 92 may be made of plush fabric. In other embodiments said cover may be made of cotton, chiffon, leather, linen, or any variation thereof. Said cover 92 may conform to said barrier assembly 40 and said base assembly 20. Said cover further includes a plurality of openings 94 that may permit the elements of said soothing assembly 80 to be shown. Said plurality of openings 94 may also permit the plurality of straps 64 to pass therethrough.

In another embodiment 100 said fall prevention barrier 10 may have a folded configuration permitting the fall prevention barrier to be folded for it to be stored and easily transported.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A fall prevention barrier, consisting essentially of:
   a. a base assembly including a first base layer, and a second base layer, said second base layer is mounted on top of said first base layer, said first base layer is made of cardboard, said second base layer is made of memory foam, said second base layer further includes a top distal end, a right distal end, a left distal end;
   b. a barrier assembly including a plurality of barriers: a top barrier, a right lateral barrier, and a left lateral barrier, said plurality of barriers is mounted onto said base assembly to form elevated barriers that are configured to stop a user to fall from the fall prevention barrier, each barrier from said plurality of barriers has a cuboid shape and is made of foam;
   c. a fastening assembly including a plurality of fasteners and a plurality of straps, said plurality of fasteners is used to join said first base layer with said second base layer, said plurality of barriers to form said top barrier, said right lateral barrier and said left lateral barrier, said plurality of straps are configured to secure a user when sleeping;
   d. a soothing assembly including a plurality of lights, a plurality of voice recorders, and a book holder, said plurality of lights, said voice recorders and said book holder are mounted in said plurality of barriers, the soothing assembly is configured to provide comfort to a user; and
   e. a cover assembly including a cover, said cover further includes a plurality of openings to permit said soothing assembly and said plurality of straps to pass therethrough, said cover conforms to said base assembly and said barrier assembly, said cover is made of plush fabric.

2. A fall prevention barrier, consisting of:
   a. a base assembly including a first base layer, and a second base layer, said second base layer is mounted on top of said first base layer, said first base layer is made of cardboard, said second base layer is made of memory foam, said second base layer further includes a top distal end, a right distal end, a left distal end;
b. a barrier assembly including a plurality of barriers: a top barrier, a right lateral barrier, and a left lateral barrier, said top barrier is mounted onto said top distal end, said right lateral barrier is mounted onto said right distal end, said left lateral barrier is mounted onto said left distal end, said top barrier, right lateral barrier and left lateral barrier form elevated barriers that are configured to stop a user to fall from the fall prevention barrier, each barrier from said plurality of barriers has a cuboid shape and is made of foam;
c. a fastening assembly including a plurality of fasteners and a plurality of straps, each fastener from said plurality of fasteners is a hook and loop fastener, said plurality of fasteners is used to join said first base layer with said second base layer, said plurality of fasteners is also used to join the plurality of barriers to form said top barrier, said right lateral barrier and said left lateral barrier, said plurality of straps are configured to secure a user when sleeping;
d. a soothing assembly including a plurality of lights, a plurality of voice recorders, and a book holder, said plurality of lights, said voice recorders and said book holder are mounted in said plurality of barriers, the soothing assembly is configured to provide comfort to a user; and
e. a cover assembly including a cover, said cover further includes a plurality of openings to permit said soothing assembly and said plurality of straps to pass therethrough, said cover conforms to said base assembly and said barrier assembly, said cover is made of plush fabric.

* * * * *